United States Patent
Brotzel et al.

(10) Patent No.: US 10,358,272 B2
(45) Date of Patent: Jul. 23, 2019

(54) REUSABLE WATERTIGHT MEDICINE CAP FOR DETECTING AND RECORDING OPENINGS AND CLOSINGS

(71) Applicant: INTELLIGENT DEVICES SEZC INC., Grand Cayman (KY)

(72) Inventors: Dean Brotzel, Ottawa (CA); Michael Petersen, Ottawa (CA); Allan Wilson, Ottawa (CA)

(73) Assignee: INTELLIGENT DEVICES SEZC INC., Grand Cayman (KY)

( * ) Notice: Subject to any disclaimer, the term of this patent is extended or adjusted under 35 U.S.C. 154(b) by 0 days.

(21) Appl. No.: 15/498,067

(22) Filed: Apr. 26, 2017

(65) Prior Publication Data

US 2017/0225854 A1    Aug. 10, 2017

Related U.S. Application Data

(63) Continuation of application No. PCT/CA2015/051100, filed on Oct. 28, 2015.

(30) Foreign Application Priority Data

Nov. 4, 2014 (CA) ................. 2869491

(51) Int. Cl.
| | |
|---|---|
| *A61J 1/03* | (2006.01) |
| *A61J 1/14* | (2006.01) |
| *A61J 7/04* | (2006.01) |
| *B65D 51/24* | (2006.01) |
| *G16H 20/00* | (2018.01) |
| *G16H 20/13* | (2018.01) |

(52) U.S. Cl.
CPC ............. *B65D 51/245* (2013.01); *A61J 1/03* (2013.01); *A61J 1/1418* (2015.05); *A61J 7/0418* (2015.05); *A61J 7/0481* (2013.01); *G16H 20/13* (2018.01); *A61J 2200/30* (2013.01); *Y02W 30/807* (2015.05)

(58) Field of Classification Search
CPC ..... B65D 51/245; A61J 7/0481; A61J 7/0418; A61J 1/03; A61J 1/1418
USPC ................................... 368/10; 705/3
See application file for complete search history.

(56) References Cited

U.S. PATENT DOCUMENTS

| | | | |
|---|---|---|---|
| 4,939,705 A | 7/1990 | Hamilton et al. | |
| 5,852,590 A | 12/1998 | de la Huerga | |

(Continued)

FOREIGN PATENT DOCUMENTS

| | | |
|---|---|---|
| WO | 0019962 A2 | 4/2000 |
| WO | 2008055821 A1 | 5/2008 |
| WO | 2013126897 A1 | 8/2013 |

OTHER PUBLICATIONS

International Search Report issued in International Application No. PCT/CA2015/051100, dated Jan. 27, 2016, 5 pages.

*Primary Examiner* — Farhana A Hoque
(74) *Attorney, Agent, or Firm* — Yakov S. Sidorin; Quarles & Brady LLP

(57) ABSTRACT

A reusable water-tight medicine cap for detecting and recording openings and closings. The cap has sealing means for engaging a rim of a bottle opening. Detection means is configured to detect the presence or absence of the bottle opening within the cap, while electronic circuitry may be included to control operations of the cap. There may be included compliance means for motivating the user to comply with medication instructions.

26 Claims, 2 Drawing Sheets

(56) References Cited

U.S. PATENT DOCUMENTS

| | | | |
|---|---|---|---|
| 2006/0218011 A1* | 9/2006 | Walker | G06F 19/3456 705/3 |
| 2013/0222135 A1* | 8/2013 | Stein | A61J 7/0409 340/540 |
| 2014/0266760 A1* | 9/2014 | Burke, Jr. | G08B 21/24 340/687 |

* cited by examiner

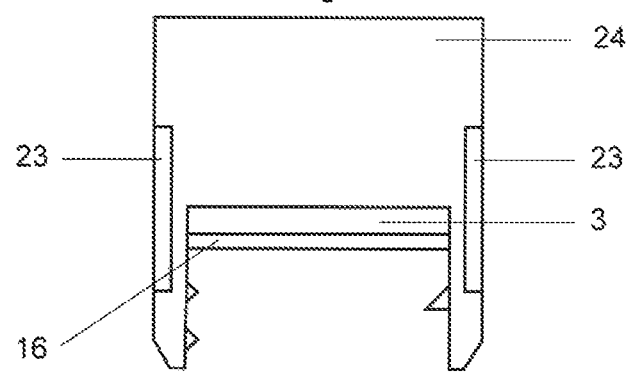
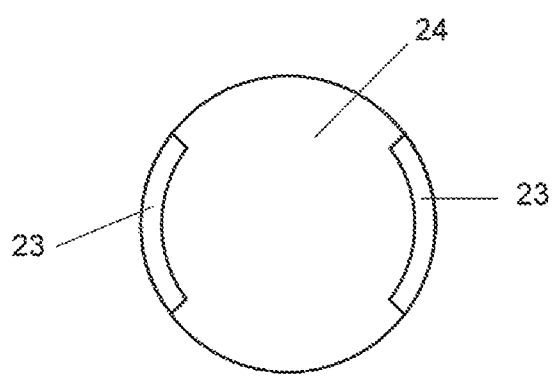

REUSABLE WATERTIGHT MEDICINE CAP FOR DETECTING AND RECORDING OPENINGS AND CLOSINGS

CROSS-REFERENCE TO RELATED APPLICATIONS

The present application is a continuation of pending International Patent Application PCT/CA2015/051100, filed on Oct. 28, 2015, which designates the United States and which in turn claims priority from the Canadian Patent Application No. 2,869,491 filed on Nov. 4, 2014. The disclosure of each of the above-referenced patent documents is incorporated by reference herein.

TECHNICAL FIELD

The present invention pertains to a reusable watertight medicine cap. In particular, the reusable watertight medicine cap includes means for detecting and recording the opening and closing of the cap. More particular, there may be included compliance means for motivating the user to comply with medication instructions.

BACKGROUND

Medication vial and bottle caps are widely used in the containment of tablets, capsules, powders, liquids and other medication forms. It is widely accepted that patients are poorly compliant in taking medication according to the recommended dosing schedule, and that such noncompliance can have serious consequences for the patient's health. Further, it is known that one large component of patient noncompliance is forgetting. Patients simply get too busy and fail to follow the medication schedule.

The idea of having a medication vial cap to remind patients to take their medication on schedule is well known. Basic to the reminder function is the requirement to monitor openings and closings of the vial as a means of inferring the patient's compliance with the prescribed regimen. This in turn requires a means of determining when the vial cap is removed. Such means are widely taught in the form of switches that determine when the cap is removed. Such switches are typically integrated into or applied to the cap.

Devices to determine bottle openings and closings are typically mechanical or electromechanical, and require means integrated in the cap to detect rotation of the cap relative to the vial. There are limitations to such devices in that they are complex, expensive to manufacture, and are not robust having limited number of open-close cycles due to their mechanical nature and moving parts.

A further limitation is that most such caps are limited to the containment of capsules, tablets and other compressed solid formats and cannot be used for powders or liquids. Vial and bottle caps generally comprise a screw-on component that houses an internal seal. Those designed to monitor patient compliance typically have two parts to the shell the upper of which contains the required electronics and is attached atop the lower component housing a snap-in clear plastic insert with screw threads for connecting to the vial and a sealing surface. Because of the requirement for a means of detecting the rotation of the cap relative to the vial and the interference of such means with the integrity of the cap's insert and/or sealing surface, such caps are not suitable for vials of liquids or powders due to the possibility of leakage.

SUMMARY

In accordance with one aspect of the present invention there is provided a cap having sealing means for engaging a rim of a bottle opening and detection means for detecting the presence or absence of the bottle opening within the cap. The cap also may comprise electronic circuitry for controlling operation of the cap.

In accordance with another aspect of the present invention there is provided a cap wherein the detection means comprises a transmitter and a receiver located on opposing internal sides of the cap.

In accordance with another aspect of the present invention there is provided a cap wherein the detection means comprises at least two metal plates located on opposing internal sides of the cap and forming a capacitor therewith.

In accordance with another aspect of the present invention there is provided a cap wherein the detection means periodically polls for detection of the presence or absence of the bottle opening.

In accordance with another aspect of the present invention there is provided a cap wherein the receiver periodically polls for a signal from the transmitter. In another aspect, the electronic circuitry periodically polls for a change in capacitance across the at least two metal plates.

In accordance with another aspect of the present invention there is provided a cap further comprising an alert unit configure to generate an indicia of full closure of the cap on the bottle opening.

In accordance with another aspect of the present invention there is provided a cap further comprising a switch to detect downward pressure applied to the cap. In a further aspect, detection of downward pressure by the switch initiates polling for the detection of the presence or absence of the bottle opening.

In accordance with another aspect of the present invention there is provided a cap wherein the electronic circuitry comprises a processor and a computer readable medium storing statements and instructions thereon that, when executed by the processor, govern the processor to track compliance of a user. In a further aspect, compliance means motivate the user to comply with medication instructions (instructions for using the bottle with medication contained therein). In yet a further aspect, the compliance means further comprises one or more of a numeric display, a pattern of LEDs, a pattern of LCDs, a colour change of an OLED, or a display of symbols. In again a further aspect, the compliance means warns the user of non-compliance by activating the alert unit.

In accordance with another aspect of the present invention there is provided a cap further comprising a transmission means to transmit compliance data (pertaining to compliance of the user with medication instructions) to an external device. In a further aspect, the external device is selected from the group consisting of a tablet, a smart phone and a computer. In yet a further aspect, the transmission means is selected from the group consisting of a USB, a wired protocol, a wireless protocol, Wi-fi and GSM.

In accordance with another aspect of the present invention there is provided a cap wherein the sealing means comprises an interior insert having screw threads dimensioned to mate with screw threads on the bottle opening. In a further aspect, the electronic circuitry further comprises a power source and a memory for storing compliance data.

BRIEF DESCRIPTION OF THE DRAWINGS

FIG. 3 shows a front view of the cap;
and
FIG. 4 shows a bottom view of the cap.

DETAILED DESCRIPTION

Figure 1:
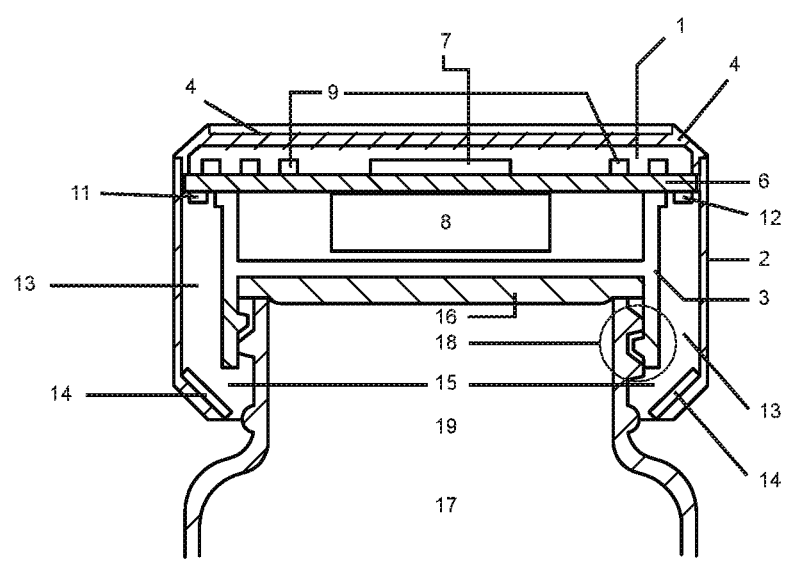
FIG. 1 shows a cross-sectional view of a cap in accordance with the present invention.
Figure 2:
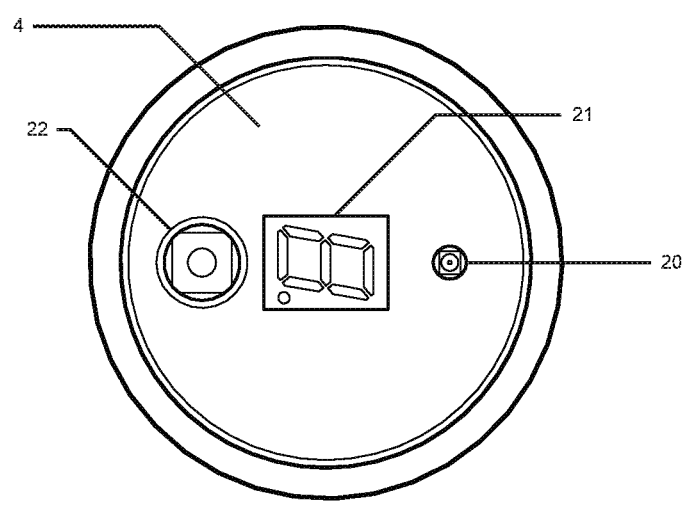
FIG. 2 shows a top view of the cap.

The present invention relates to a cap that detects openings and closings of any standard medication vial or bottle without recourse to mechanical or electromechanical switches, while providing a watertight seal for the contents.

The cap is a self-contained device, has no electromechanical moving parts, has a high degree of reliability and is therefore robust in terms of use cycles, and does not interfere with the sealing and resealing of the vial or bottle when the cap is replaced thus allowing for use with liquid or powder contents.

The device comprises a lower plastic housing 2 that contains an industry standard clear or translucent plastic insert portion 3 that is interior to the cap and has screw threads for attaching to a vial 17 or bottle. The insert portion snaps into the housing and also has a seal 16 that mates 18 with the rim of the vial 17 when the cap is screwed in place to seal the contents in the vial 17. The cap also has an upper plastic housing with a well 1 in its upper aspect to contain its electronics mounted on a circular PCB 6 shaped to fit snugly in the well 1 by adhesive or friction fit. The electronics may comprise various surface mounted components 9 and may include a power source, CPU 7, memory, and optional display, reminder and control features including but not limited to visual LED 20 (light emitting diode) and OLED (organic light emitting diode), auditory and tactile devices and switches (buttons) 22. For example, the switches 22 enable a user to reset the cap. The well 1 is covered by a snap or glue on cover 4 designed around the desired reminder, display 21 and control features.

In one variant the cap's cover 4 is translucent to allow light indicators to show through or to accommodate an OLED display on its surface.

On the underside of the PCB 6 at the respective extremities of one diameter are mounted an infrared (IR) or other frequency spectrum transmitter 11 and an associated receiver 12. Each of the IR devices communicates with a vertical lightproof tunnel 13 having its aperture 15 located at its lower extremity and facing the other aperture 15 across the neck 19 of the opaque vial 17 or bottle for which it is designed.

When no vial is present between the apertures 15 the IR transmitter's signal can cross from the transmitter aperture to the receiver aperture and thence to the receiver 12. When the cap is screwed on to an opaque vial or bottle the IR beam is interrupted and the receiver 12 does not detect a signal, indicating the bottle closed state.

As power is limited for the self-contained devices, in one embodiment the device saves power by having the IR or other receiver poll the transmitter's signal at intervals the frequency of which is inversely correlated with power use.

In a further variation the CPU interrupts polling if a continuous cap-off pattern exceeds a specified interval.

In a further power-saving example the cap incorporates a highly sensitive mechanical vibration sensor to indicate if the cap and vial are being handled or not. If there is no vibration due to handling, the receiver does not poll for a signal, conserving power.

In another embodiment the apertures 15 of the light tunnels 13 incorporate angled reflectors or lenses 14 to focus and enhance the IR beam in the direction of the receiver's tunnel 13 and thence to the receiver allowing for the use of a lower powered IR source.

In one embodiment the cap includes an alert unit or device providing, in operation, a tactile (vibration), visual (LED) or auditory (beep) alert signal when the cap is fully closed to indicate to the user that it has been reset as closed.

In another embodiment the IR or other signal comprises a coded data protocol to prevent spurious opening reports as a result of external light sources.

A further embodiment is designed for child resistant (CR) cap applications that require downward pressure on the cap to open it. A switch (not shown) is incorporated in the cap to detect such downward opening pressure as a means of inferring an opening event and thus medication usage, and to produce an output signal representing successful detection.

In a further embodiment the CR requiring downward pressure on the cap for opening also functions as a switch to control the CPU's polling. When downward pressure is applied to the cap, the signal output from a switch incorporated in the cap turns on the polling process. This avoids unnecessary polling and thus power consumption when the cap is not in active use.

In another embodiment the cap housing has two identical curved conductive metal plates 23 attached at the internal extremities of one diameter. The plates form a capacitor with the vial or bottle neck 19 acting as a dielectric. Removing the cap 24 from the bottle changes the capacitance, which change is detected and recorded as an opening event by the CPU.

In one embodiment the cap's CPU is programmed with dosing intervals or other pharmacokinetic (PK) information. The use data collected by opening events are compared to the PK data to determine the extent to which the use data are consistent with the PK data.

In a further embodiment the cap's CPU is programmed with an algorithm to track the patient's compliance and the cap can display this by way of motivating the patient's behavior as, for example, continually updating, rating and displaying the patient's medication-taking level of compliance.

In a further example, the cap can display compliance data numerically, by patterns of LEDs or LCDs crystal display), by colour changes via OLEDs and/or by symbols or other means.

In another embodiment the cap's CPU is programmed to continually compare the most recent opening to previous openings using a dynamic algorithm and to compare the patient's compliance pattern to a preprogrammed ideal PK pattern. Using regression analysis or other widely taught trend analytical techniques the CPU develops a dynamic algorithm to predict problematic trends in the patient's compliance. Warnings can then be provided using the cap's output visual, auditory or tactile device(s) to alert the user to maladaptive medication-taking trends and potential problems.

In another embodiment the cap is additionally equipped with the ability to be plugged into a computer using USB or other wired protocol. The compliance data can be summarized and displayed in graphic format to motivate the patient.

In a further embodiment, the cap incorporates means of emitting an RF signal that permits communication with an external smart device such as a tablet or phone using RFD, Bluetooth, NFC, sigFox, qual2 or other data transmission protocol. Such means would include an RFID tag or an antenna or other similar transmission device. These devices can be used to display reminders, compliance summaries or other information via apps.

In a further embodiment the cap can incorporate the ability to communicate by GSM (Groupe Spécial Mobile) to devices which can be used to display reminders, compliance summaries or other information via graphic user interfaces or apps.

In a valiant, other parties of interest other than the user may be given permission to access the cap's data via apps on smart devices or computers in the interests of monitoring the user's compliance with prescribed medication and detecting maladaptive patterns of use.

In another embodiment the cap can communicate wirelessly by Wi-Fi or GSM to an app forming part of a larger iHealth network from which the user and her designate(s) can access the data to receive motivational feedback and warnings about maladaptive medication-taking patterns and assessing the need for early intervention to prevent health deterioration. In one implementation, such communication is effectuated with an antenna. Wireless communication means include Capacitive Coupled, RFID, HF, UHF, Bluetooth and NFC.

The cap is reusable and can be returned to the pharmacy for reuse or retained to be reused on a subsequent refill of the same medication for the same patient. Any power source (e.g. battery 8) can be replaced as required.

It will be appreciated by one skilled in the art that variants can exist in the above-described arrangement and application of the cap. The specific examples provided herein relate to a reusable watertight cap for a medication vial or bottle without recourse to a mechanical switch; however the materials, methods of application and arrangements of the invention can be applied to other types of packaging and contents.

The scope of the claims should not be limited by the preferred embodiments set forth in the examples, but should be given the broadest interpretation consistent with the description as a whole.

What is claimed is:

1. A cap for a bottle, the cap having an outer cylindrical wall and an inner cylindrical wall, the cap comprising:
   a sealing means for engaging a rim of a bottle, said sealing means including the inner cylindrical wall;
   a detection means for detecting presence or absence of the bottle within the cap; and
   an electronic circuitry configured to control an operation of the cap;
   wherein the detection means comprises a transmitter and a receiver located on opposing internal sides of the cap,
   wherein the cap is dimensioned to define a path for a signal, generated by the transmitter, between the transmitter and the receiver, said path including a first path portion across an opening formed by a first circumferential edge of the outer cylindrical wall.

2. The cap of claim 1, wherein the detection means is configured to periodically poll to detect presence or absence of the bottle.

3. The cap of claim 1, wherein the receiver is configured to periodically poll for a signal from the transmitter.

4. The cap of claim 1, further comprising an alert unit configured to indicate full closure of the cap on the bottle.

5. The cap of claim 1, further comprising a switch configured to detect downward pressure applied to the cap and generate an output signal representing successful detection of said downward pressure.

6. The cap of claim 5, configured to trigger an operation of said detection means in response to generation of said output signal.

7. The cap of claim 1, wherein the electronic circuitry comprises a processor and a computer-readable medium configured to store statements and instructions thereon that, when executed by the processor, govern the processor to track compliance of a user with instructions for using the bottle.

8. The cap of claim 7, further comprising a compliance means for motivating the user to comply with the instructions.

9. The cap of claim 8, wherein the compliance means further comprises one or more of a numeric display, a pattern of LEDs, a pattern of LCDs, a colour change of an OLED, and a display of symbols.

10. The cap of claim 9, further comprising an alert unit in operable communication with the compliance means, wherein the compliance means is configured to warn the user of non-compliance by activating the alert unit.

11. The cap of claim 8, further comprising a transmission means configured to transmit compliance data, representing compliance of the user with the instructions, to an external device, wherein said compliance data are configured to establish communication between the transmission means and the external device.

12. The cap of claim 11, wherein the external device is selected from the group consisting of a tablet, a smart phone, and a computer.

13. The cap of claim 11, wherein the transmission means is selected from the group consisting of a USB, a wired protocol, a wireless protocol, Wi-fi, and GSM.

14. The cap of claim 1, wherein the sealing means comprises screw threads, on an inner portion of the inner cylindrical wall, dimensioned to mate with threads on the bottle.

15. The cap of claim 14, wherein the electronic circuitry further comprises a power source and a tangible non-transitory memory.

16. The cap of claim 1, further comprising a transmitter aperture and a receiver aperture, each of which is located by the first circumferential edge and dimensioned to transmit the signal along the path.

17. The cap of claim 16, comprising a first tunnel connecting the transmitter to the transmitter aperture and a second tunnel connecting the receiver to the receiver aperture.

18. The cap of claim 1, wherein said transmitter is configured to generate an optical signal and said receiver is configured to detect said optical signal.

19. The cap of claim 1, wherein the path includes a second path portion in a gap between the outer cylindrical wall and the inner cylindrical wall.

20. The cap of claim 1, wherein the electronic circuitry comprises a processor and a computer-readable medium configured to store statements and instructions thereon that, when executed by the processor, govern the processor to track compliance of a user with medication instructions.

21. A cap for a bottle, the cap having a cylindrical wall and comprising:
   sealing means dimensioned to engage the bottle;
   detection means for detecting presence or absence of the bottle within the cap; and
   electronic circuitry operably connected with the detections means and configured to control an operation of the cap;

wherein the detection means includes at least two curved conductive metal plates located on opposing internal surfaces of the cylindrical wall,
said two metal plates configured to form a capacitor in which, when the bottle is present within the cap, the bottle forms at least a part of a dielectric medium of the capacitor, to enable the detection means to detect the presence of the bottle based on changes in capacitance of said capacitor.

22. The cap of claim 21, wherein the electronic circuitry is configured to periodically poll for a change of the capacitance of said capacitor.

23. The cap of claim 21, further comprising an alert unit configured to provide indicia of full closure of the cap on the bottle.

24. The cap of claim 21, further comprising a switch configured to detect a downward pressure applied to the cap and generate an output signal representing successful detection of said downward pressure.

25. The cap of claim 24, wherein the electronic circuitry is configured to trigger an operation of said detection means in response to generation of said output signal.

26. The cap of claim 21, comprising:
an outer cylindrical wall and an inner cylindrical wall separated from the outer cylindrical wall by a gap.

* * * * *